United States Patent
Enna et al.

(10) Patent No.: US 6,316,677 B1
(45) Date of Patent: Nov. 13, 2001

(54) PRODUCTION PROCESS OF BISPHENOL COMPOUNDS

(75) Inventors: Masahiro Enna; Naoshi Nagai, both of Kanagawa; Toshiyuki Isaka, Yamaguchi, all of (JP)

(73) Assignee: Mitsui Chemicals, Inc. (JP)

( * ) Notice: Subject to any disclaimer, the term of this patent is extended or adjusted under 35 U.S.C. 154(b) by 0 days.

(21) Appl. No.: 09/270,016

(22) Filed: Mar. 16, 1999

(30) Foreign Application Priority Data

Mar. 24, 1998 (JP) .................................................. 10-076081

(51) Int. Cl.$^7$ ..................................................... C07C 39/12
(52) U.S. Cl. ............................................ 568/722; 568/723
(58) Field of Search ..................................... 568/722, 723, 568/718, 724, 719

(56) References Cited

U.S. PATENT DOCUMENTS

| | | | | |
|---|---|---|---|---|
| 4,191,843 | * | 3/1980 | Kwantes | 568/722 |
| 4,766,254 | * | 8/1988 | Faler | 568/722 |
| 4,950,807 | * | 8/1990 | Iimuro | 568/722 |

FOREIGN PATENT DOCUMENTS

| | | | |
|---|---|---|---|
| 4014992 | * | 11/1991 | (DE) . |
| 1377227 | * | 12/1974 | (GB) . |
| 63-303939 | * | 12/1988 | (JP) . |

* cited by examiner

Primary Examiner—Michael L. Shippen
(74) Attorney, Agent, or Firm—Burns, Doane, Swecker & Mathis, L.L.P.

(57) ABSTRACT

A process for the production of a bisphenol compound comprising:

a step for reacting a phenolic compound (a) with at least one compound (b) selected from the group consisting of dialkenylbenzene compounds, bis(hydroxyalkyl)benzene compounds and (hydroxyalkyl)-alkenylbenzene compounds or at least one compound (c) selected from the group consisting of monoalkenylphenolic compounds and mono(hydroxyalkyl)phenolic compounds in the presence of an acidic catalyst to obtain a reaction mixture containing said bisphenol compound, a step for neutralizing the reaction mixture with an anion exchange resin, a step for removing a remaining phenolic compound from the reaction mixture to concentrate the neutralized reaction mixture, and a step for isolating the bisphenol compound from the resulting concentrated mixture.

This process enables to produce a bisphenol compound, which is useful for preparing raw materials of thermoplastic polymers, surface-active agents and stabilizers.

6 Claims, No Drawings

PRODUCTION PROCESS OF BISPHENOL COMPOUNDS

BACKGROUND OF THE INVENTION

The present invention relates to a process of the production of bisphenol compounds, which are useful as raw materials of thermoplastic polymers, surface-active agents and stabilizers.

With respect to the process of producing a bisphenol compound, German Patent No. 2,534,558 and JP 58-13528 A (Tokkaisho) each disclose a process in which an α, α"-dihydroxydiisopropylbenzene or a diisopropenylbenzene is reacted with a phenol in the presence of an acidic catalyst such as an ion exchange resin.

In these processes, however, there is a problem that the isolation yield of a bisphenol compound, the intended product, from a reaction mixture is low. This is because an acid, isolated from an ion exchange resin in the reaction, generates a high order adduct of a bisphenol compound when the reaction mixture is heated to remove phenol after the reaction. To solve the problem, JP 8-13770 B (Tokkohei) discloses a process in which excess phenol is distilled off from the reaction mixture containing a bisphenol compound after neutralization by adding a base such as disodium hydrogen phosphate. Then, the resulting mixture is washed with water after the removal of phenol. The bisphenol compound is isolated through crystallization and drying.

This process prevents the production of high order adducts of bisphenol compound but needs inorganic base aqueous solutions for neutralization when bisphenol compounds are isolated from the reaction mixture and purified as the intended products. Moreover, there is a problem in that waste water that contains phenol is generated inevitably and its treatment costs are very high.

JP 5-44932 B (Tokkohei) discloses a process in which a small amount of hydrogen chloride remaining in bisphenol A is removed with anion exchange resins that have pyridyl groups and excellent thermal stability at temperatures higher than 100° C. The gazette does not disclose bisphenol M that is produced according to the present invention, and discloses that basic ion exchange resins having secondary or tertiary amines as exchange groups cannot be used in the production of bisphenol A.

DESCRIPTION OF THE INVENTION

The present inventors recognized that there were the above-mentioned problems in the production of bisphenol compounds and studied separation and purification steps to solve the above-mentioned problems.

The present inventors thought that neutralization could be carried out by using an anion exchange resin such as Amberlist A-21 when a free acid generated in the reaction is removed. Because bisphenol A, as disclosed in JP 5-44932 B, is produced by removing hydrogen chloride without existence of solvent, the reactant product must be heated higher than 100° C. for treating in a fused state.

Therefore, it was impossible to use basic ion exchange resin having at least one group of amino group or quaternary ammonium salt group in the process of JP 5-44932.

The present inventors have found that when a step for neutralization of reaction products is done in the presence of at least one solvent selected from the group consisting of aromatic hydrocarbon compounds and aliphatic hydrocarbon compounds, because it is possible to deal with a reaction product at lower than 100° C., it is possible to use an anion exchange resin in the neutralization step.

Thus the use of an inorganic base aqueous solution became unnecessary and a process free from waste water could be constructed. They treated the reaction mixture with an anion exchange resin in place of conventional alkali washing, and found that the thus obtained bisphenol compounds were usable offering no problem of quality and the isolation yield was satisfactory.

Accordingly, the present invention includes the following items.

(1) A process for the production of a bisphenol compound comprising:

a step for reacting a phenolic compound (a) with at least one compound (b) selected from the group consisting of dialkenylbenzene compounds, bis(hydroxyalkyl)benzene compounds and (hydroxyalkyl)-alkenylbenzene compounds or at least one compound (c) selected from the group consisting of monoalkenylphenolic compounds and mono(hydroxyalkyl) phenolic compounds in the presence of an acidic catalyst to obtain a reaction mixture containing said bisphenol compound, a step for neutralizing said reaction mixture with an anion exchange resin, a step for removing the phenolic compound remaining in said reaction mixture to concentrate said neutralized reaction mixture, and a step for isolating said bisphenol compound from said concentrated mixture.

(2) A process as described above in (1), wherein said acidic catalyst is a cation exchange resin.

(3) A process as described above in (1), wherein said step for neutralizing is carried out in at least one solvent selected from the group consisting of aromatic hydrocarbon compounds and aliphatic hydrocarbon compounds.

(4) A process as described above in (1), wherein said reaction is carried out in at least one solvent selected from the group consisting of aromatic hydrocarbon compounds and aliphatic hydrocarbon compounds.

(5) A process as described above in (1), wherein said anion exchange resin is an ion exchange resin having at least one basic group selected from the group consisting of amino groups and quaternary ammonium salts.

(6) A process as described above in (1), wherein said isolation is carried out by crystallization.

(7) A process as described above in (6), wherein toluene or xylene is used as the solvent of said crystallization.

The preparation process of bisphenol compounds, related to the present invention, will concretely be described.

With respect to the preparation process of bisphenol compounds related to the present invention, illustrative examples of the raw material of the reaction include a phenolic compound (a), at least one compound (b) selected from the group consisting of dialkenylbenzene compounds, bis(hydroxyalkyl)benzene compounds and (hydroxyalkyl)alkenylbenzene compounds or at least one compound (c) selected from the group consisting of monoalkenylphenolic compounds and mono(hydroxyalkyl)phenolic compounds.

In this case, illustrative examples of the phenolic compound include aromatic hydrocarbons having a phenolic hydroxyl group, such as phenol, o- or p-cresol, o- or p-ethylphenol, m-isopropylphenol, 2,6-xylenol, 3,5-xylenol, 1-naphthol and 2-naphthol.

Illustrative examples of the alkenyl group and the hydroxy group of the above-mentioned dialkenylbenzene compounds, (hydroxyalkyl)alkenylbenzene compounds and monoalkenylphenolic compounds (b), and bis (hydroxyalkyl)benzene compounds, (hydroxyalkyl) alkenylbenzene compounds and mono(hydroxyalkyl) phenolic compounds (c) include 1-alkenyl groups preferably having 1–6 carbon atoms, such as vinyl group, isopropenyl group, 1-ethylvinyl group and 1-propylvinyl group, and include 1-hydroxyalkyl groups preferably having 1–6 carbon atoms, such as hydroxymethyl group, 1-hydroxyethyl group, 1-hydroxy-1-methylethyl group, 1-hydroxy-1-methylpropyl group and 1-hydroxy-1-ethylpropyl group.

The substitution format of the above-mentioned dialkenylbenzene compounds, bis(hydroxyalkyl)benzene compounds, (hydroxyalkyl)alkenylbenzene compounds, monoalkenylphenolic compounds and mono(hydroxyalkyl) phenolic compounds may be any of the o-, m- and p-substitutions.

In the above-mentioned compound (b), reacted with the phenolic compound (a) in the present invention, illustrative examples of the dialkenylbenzene compounds include divinylbenzenes, diisopropenylbenzenes, isopropenylvinylbenzenes and bis(1-ethylvinyl)benzenes. Illustrative examples of the bis(hydroxyalkyl)benzene compounds include bis(hydroxymethyl)benzenes, bis(1-hydroxyethyl) benzenes, bis(1-hydroxy-1-methylethyl)benzenes and bis(1-hydroxy-1-methylpropyl)benzenes. Illustrative examples of the (hydroxyalkyl)alkenylbenzene compounds include (1-hydroxyethyl)vinylbenzene, (1-hydroxy-1-methylethyl)-vinylbenzene, (1-hydroxyethyl)-isopropenylbenzene and (1-hydroxy-1-methylpropyl)-(1-ethylvinyl)benzene.

In the above-mentioned compound (c), reacted with the phenolic compound (a) in the present invention, illustrative examples of the monoalkenylphenolic compounds include vinylphenol, isopropenylphenol and (1-ethylvinyl)phenol. Illustrative examples of the mono(hydroxyalkyl)phenolic compounds include hydroxymethylphenol, 1-hydroxyethylphenol, 1-hydroxy-1-methylethylphenol and (1-hydroxy-1-methylpropyl)phenol.

In the above-mentioned compound (b) and compound (c), reacted with the phenolic compound (a) in the present invention, any one of compounds selected from one group may be used alone, or at least two may be used in the form of a mixture. An illustrative example of using a mixture, for example, is a method in which a phenolic compound (a) is reacted with a mixture of compound (b) consisting of diisopropenylbenzene, bis(1-hydroxy-1-methylethyl) benzene and (1-hydroxy-1-methylethyl)-isopropenylbenzene.

When the above-mentioned phenolic compound (a) is reacted with the above-mentioned compound (b) or the above-mentioned compound (c) in the presence of an acidic catalyst according to the present invention, a reaction mixture containing a bisphenol compound is obtained. Illustrative bisphenols are given hereunder. That is, when the above-mentioned phenolic compound (a) and the above-mentioned compound (b) are used as the raw materials of the reaction, illustrative examples of the bisphenol compound include α, α"-bis(4-hydroxyphenyl)-1,3-diisopropylbenzene (bisphenol M), α, α"-bis(4-hydroxyphenyl)-1,4-diisopropylbenzene (bisphenol P), α, α"-bis(4-hydroxy-3-methylphenyl)-1,3-diisopropylbenzene, α, α"-bis(4-hydroxy-3-methylphenyl)-1,4-diisopropylbenzene, α, α"-bis(4-hydroxy-3,5-dimethylphenyl)-1,3-diisopropylbenzene and α, α"-bis(4-hydroxy-3,5-dimethylphenyl)-1,4-diisopropylbenzene.

When the above-mentioned phenolic compound (a) and the above-mentioned compound (c) are used as the raw materials of the reaction, illustrative examples of the bisphenol compound include 2,2-bis(4-hydroxyphenyl)propane, 2,2-bis(4-hydroxyphenyl)butane, 1,1-bis(4-hydroxyphenyl) ethane, 2,2-bis(4-hydroxy-3-methylphenyl)propane, 2,2-bis (4-hydroxy-3,5-dimethylphenyl)propane and 2-(3-hydroxyphenyl)-2-(4-hydroxyphenyl)propane.

Illustrative examples of the acidic catalyst include sulfuric acid, hydrochloric acid, hydrogen chloride gas, boron trifluoride, hydrogen fluoride, trifluoroacetic acid, acid clay, heteropolyacid such as tungstophosphoric acid, and cation exchange resins. Cation exchange resins are preferred from the viewpoint of easy recovery after completion of the reaction.

Illustrative examples of the cation exchange resin include ion exchange resins having an acidic group, such as a sulfo group or a carboxy group, and more specifically Amberlist-15 (Rohm and Haas Co. Ltd.), and Diaion SK-LB, SK-102 to -106, PK-208 and PK-212 (Mitsubishi Chemical Corp.).

The reaction of the phenolic compound (a) with at least one compound (b) selected from the group consisting of dialkenylbenzene compounds, bis(hydroxyalkyl)benzene compounds and (hydroxyalkyl)alkenylbenzene compounds or at least one compound (c) selected from the group consisting of alkenylphenolic compounds and mono (hydroxyalkyl)phenolic compounds is usually carried out in a nitrogen atmosphere in the presence of 1 to 100 molar equivalents, and preferably 2 to 50 molar equivalents more prefebaly 5–30 molar equivalents, of the phenolic compound (a) per molar equivalent of the above-mentioned compound (b) or (c), usually with the cation exchange resin being 0.01 to 10 parts by weight, and preferably 0.1 to 1 part by weight, per part by weight of the above-mentioned compound (b) or (c).

When the reaction is carried out in a solvent according to the present invention, the reaction proceeds smoothly and therefore is preferred. Illustrative examples of the solvent include aromatic hydrocarbons such as benzene, toluene, ethylbenzene, isopropylbenzene and xylene and aliphatic hydrocarbons such as hexane and heptane. Of them, toluene, xylene, hexane and heptane are preferred. These solvents may be used in combination. The solvent is used within a range of 0.1 to 100 parts by weight, and preferably 1–10 parts by weight, per part by weight of the above-mentioned compound (b) or (c).

The phenolic compound (a) is used in excess of the equivalent of the compound (b) or (c) and the solvent is used in the reaction, which can prevent position isomers of the bisphenol compound and high order adducts of the bisphenol compound from being by-produced. When the high order adducts of the bisphenol compound are reduced in by-production, the bisphenol compound is preferably increased in yield.

The above-mentioned substrates, acidic catalysts and solvents may be charged en bloc to carry out the reaction. It is preferred to gradually feed the above-mentioned compound (b) or (c) into a mixture consisting of the phenolic compound (a), catalyst and solvent, particularly after the above-mentioned compound (b) or (c) is diluted with the above-mentioned solvent.

The feed time is usually within a range of 0.01 to 100 hours, and preferably 0.1 to 10 hours, and the feed temperature is usually within a range of −50 to 200° C., and preferably 0 to 100° C.

After completion of the feed, the post-reaction is carried out. The post-reaction is carried out at a temperature of −50 to 200° C., and preferably 0 to 100° C., for a period of time of 0.01 to 100 hours, and preferably 0.1 to 10 hours. When the cation exchange resin is used as the catalyst, the cation exchange resin can be separated by filtration after the reaction. One of the solvents illustrated as the reaction solvent may suitably be added into the reaction mixture to facilitate the filtration.

Neutralization is carried out to remove acids generated in the reaction. In a conventional method, a 0.1–30% by weight aqueous solution of an inorganic base, such as disodium hydrogenphosphate or dipotassium hydrogenphosphate is used. In the present invention, neutralization is carried out using an anion exchange resin and therefore waste water is not generated. Illustrative examples of the anion exchange resin include ion exchange resins having basic groups, such as amino groups ($-NH_2$, $-NHR$ and $-NR_2$, wherein R is an hydrocarbon group such as an alkyl group), or quaternary ammonium salts. Concrete examples thereof include Amberlist A-21, A-26 and A-27 (Rohm and Haas Co. Ltd.). Of them, ion exchange resins having at least one basic group selected from the group consisting of the above-mentioned amino groups and quaternary ammonium salts are preferred. Concrete examples thereof include Amberlist A-21. Neutralization is usually carried out at temperatures of 20 to 100° C., and preferably 50 to 80° C.

Illustrative neutralization methods include a method in which a reaction mixture is mixed with an anion exchange resin under agitation and a method in which a reaction mixture is passed through a column packed with an anion exchange resin. One of solvents given as the reaction solvent may suitably be added into the reaction mixture to neutralize the reaction mixture easily.

The amount of the anion exchange resin is not specially limited so long as the acids generated in the reaction are neutralized. The anion exchange resin is used within a range of 0.1 to 1 part by weight per part by weight of the above-mentioned compound (b) or (c).

After the neutralization, the anion exchange resin is removed by filtration. Solvent and unreacted phenolic compounds are removed from the filtrate by distillation, and then crystallization is carried out.

Crystallization is usually carried out using 0.1 to 10 parts by weight of the solvent per part by weight of the obtained bisphenol compound. Illustrative examples of the solvent include aromatic hydrocarbons such as toluene, xylene and ethylbenzene. Of these three, xylene is preferred because large amounts of impurities are soluble in it while small amounts of the bisphenol compound are soluble in it.

The substitution format of xylene may be any of the o-, m- and p-substitutions. A mixture of these substitution products is available. Moreover, 1 to 10% by weight of water is also added into these solvents. This is because water reduces the solubility of the bisphenol compound in the solvent and increases the recovery yield of it by crystallization.

In crystallization, usually, the bisphenol compound is dissolved in the above-mentioned solvent at a temperature of 30 to 150° C., and preferably 50 to 100° C., and then the solution temperature is gradually reduced to a temperature of –50 to 50° C., and preferably 0 to 50° C., in a time period of 0.1–10 hours, preferably 0.5–5 hours.

After the solution temperature is reduced, the intended solid product is recovered by separation of solid and liquid.

Above-mentioned crystallization is carried out once to 10 times and preferably twice to 4 times.

Furthermore, the mother liquor of crystallization is added into the reaction system or one of the preceding crystallization systems in order to improve the isolation yield of bisphenol compound. For example, ¼ to ¾ of the primary crystallization mother liquor is added into the reaction system, and ½ to the total of the secondary crystallization mother liquor is added into the primary crystallization system. Even in this case, the bisphenol compound can be obtained with its quality being kept while the isolation yield of bisphenol compound can be increased.

After the crystallization, the resulting slurry is filtrated, and the resulting crystal is dried under reduced pressure to obtain the bisphenol compound, the intended product.

Embodiments will be illustrated hereunder but the scope of the present invention is not limited by these embodiments at all.

EXAMPLE 1

(Reaction)

A 500-ml three-neck reactor was charged with Amberlist-15 (7.5 g, 2.6 mmols), phenol (178.5 g, 633 mmols) and p-xylene (60 ml). The contents were heated up to 80° C. in nitrogen atmosphere. Under agitation, a mixture of m-diisopropenylbenzene (m-DIPeB, 15.0 g, 31.5 mmols) and p-xylene (60 ml) was fed thereto over 3 hours at 80° C. After completion of the feed, agitation was carried out at 80° C. for 10 minutes and then Amberlist-15 was removed by filtration. The filtrate was analyzed by liquid chromatography. Bisphenol M ($\alpha$, $\alpha''$-bis(4-hydroxyphenyl)-1,3-diisopropylbenzene, 30.5 g, yield 93%), the intended product, and the o, p-product, the position isomer of bisphenol M ($\alpha$-(4-hydroxyphenyl)-$\alpha''$-(2-hydroxyphenyl)-1,3-diisopropylbenzene, 1.67 g, yield 5.1%), were obtained.

(Purification)

Amberlist A-21 having trimethyl amino group (7.5 g) was charged into the obtained reaction mixture and the contents were agitated at 60° C. for 1 hour. Amberlist A-21 was removed by filtration and then the filtrate was heated under reduced pressure to remove p-xylene and phenol. P-xylene (120 g) containing 3% by weight of water was added into the concentrated liquid after removal. The resulting mixture was heated up to 90° C. to dissolve precipitates. After dissolution, agitation was carried out at 90° C. for 1 hour and then the temperature of the solution was lowered to 40° C. over 1.5 hours. During the cooling, bisphenol M was found to crystallize out at 55° C. or lower. After completion of the cooling, bisphenol M was removed by filtration and washed with p-xylene (20 g). The bisphenol M recovered was dissolved in 100 g of p-xylene containing 3% by weight of water to again carry out crystallization, filtration and washing. Then, the obtained crystal was dried at 100° C. at 2.7 kPa (20 mm Hg) for 16 hours to isolate bisphenol M (22.7 g, yield 69%, purity 99.6%, melting point 137.5 to 138.0° C.).

EXAMPLE 2

The primary crystallization mother liquor, generated in Example 1, was concentrated and ⅔ of the resulting liquid was recovered to the reaction system. Furthermore, the total of the secondary crystallization mother liquor was used as the primary crystallization solvent to carry out the same operations as those in Example 1 so that bisphenol M was isolated (26.3 g, yield 80%, purity 99.6%, melting point 137.5 to 138.0° C.).

EXAMPLE 3

The same reaction and purification operations as those in Example 1 were carried out by substituting toluene for p-xylene, so that bisphenol M was obtained in reaction (30.4 g, yield 93%) and in the isolation (18.6 g, yield 57%, purity 99.5%). Furthermore, the o, p-product was by-produced (1.48 g, yield 4.5%).

EXAMPLES 4–7

The same reaction operations as those in Example 3 were carried out without a solvent on condition that the amount of phenol and feed temperature were changed, and the results are shown in Table 1. Xylene was used in the purification operation as a solvent.

TABLE 1

| Example | Phenol amount (eq) | Feed Temp. (° C.) | Bis-M reaction yield (%) | Bis-M isolation yield (%) | o, p-product reaction yield (%) |
|---|---|---|---|---|---|
| 4 | 13 | 80 | 80 | 50 | 10.0 |
| 5 | 20 | 80 | 82 | 52 | 6.1 |
| 6 | 20 | 60 | 75 | 49 | 2.9 |
| 7 | 20 | 100 | 72 | 45 | 8.9 |

EXAMPLES 8–12

The same operations as those in Example 3 were carried out on condition that the amount of phenol was changed, and the results are shown in Table 2.

TABLE 2

| Example | Phenol amount (eq) | Bis-M reaction yield (%) | Bis-M isolation yield (%) | o, p-product reaction yield (%) |
|---|---|---|---|---|
| 8 | 6 | 80 | 52 | 10.1 |
| 9 | 10 | 81 | 50 | 9.5 |
| 10 | 15 | 87 | 54 | 8.5 |
| 11 | 25 | 91 | 57 | 7.7 |
| 12 | 30 | 91 | 57 | 7.1 |

EXAMPLE 13

A 500-ml three-neck reactor was charged with amberlist-15 (7.5 g, 2.6 mmols), phenol (178.5 g, 633 mmols) and toluene (30 ml). The contents were heated up to 80° C. in nitrogen atmosphere. Under agitation, a mixture of m-diisopropenylbenzene (m-DIPeB, 15.0 g, 31.5 mmols) and toluene (30 ml) was fed thereto over 3 hours at 80° C. After completion of the feed, agitation was carried out at 80° C. for 10 minutes and then Amberlist-15 was removed by filtration. The filtrate was analyzed by liquid matography. Bisphenol M ($\alpha$, $\alpha$"-bis(4-hydroxyphenyl)-1,2-diisopropylbenzene, 28.8 g, yield 88%), the intended product, and the o,p-product, the position isomer of bisphenol M ($\alpha$-(4-hydroxyphenyl)-$\alpha$"-(2-hydroxyphenyl)-1,3-diisopropylbenzene, 2.79 g, yield 8.5%), were obtained. After completion of the same aftertreatment and purification operations as those in Example 3, bisphenol M was isolated (17.7 g., isolation yield 54%, purity 99.6%).

EXAMPLE 14

A 500-ml three-neck reactor was charged with Amberlist-15 (7.5 g, 2.6 mmols), phenol (178.5 g, 633 mmols) and hexane (60 ml). The contents were heated up to 80° C in nitrogen atmosphere. Under agitation, a mixture of m-diisopropenylbenzene (m-DIPeB, 15.0 g, 31.5 mmols) and hexane (60 ml) was fed thereto over 3 hours at 80° C. After completion of the feed, agitation was carried out at 80° C. for 10 minutes and then Amberlist-15 was removed by filtration. The filtrate was analyzed by liquid chromatography. Bisphenol M ($\alpha$, $\alpha$"-bis(4-hydroxyphenyl)-1,3-diisopropylbenzene, 29.6 g, yield 90%), the intended product, and the o,p-product, the position isomer of bisphenol M ($\alpha$-(4-hydroxyphenyl)-$\alpha$"-(2-hydroxyphenyl)-1,3-diisopropylbenzene, 2.43 g, yield 7.4%), were obtained.

After completion of the same aftertreatment and purification operations using p-xylene as those in Example 1, bisphenol M was isolated (22.0 g., isolation yield 67%, purity 99.5%).

EXAMPLE 15

A 500-ml three-neck reactor was charged with Amberlist-15 (7.5 g, 2.6 mmols), phenol (119.0 g, 422 mmols) and toluene (60 ml). The contents were heated up to 80° C. in nitrogen atmosphere. Under agitation, a mixture of 1,3-bis (1-hydroxy-1-methylethyl)benzene (m-DioL, 18.4 g, 31.5 mmols), phenol (59.5 g, 211 mmols) and toluene (60 ml) was fed thereto over 3 hours at 80° C. After completion of the feed, agitation was carried out at 80° C. for 10 minutes and then Amberlist-15 was removed by filtration. The filtrate was analyzed by liquid chromatography. Bisphenol M ($\alpha$, $\alpha$"-bis(4-hydroxyphenyl)-1,3-diisopropylbenzene, 27.3 g, yield 83%), the intended product, and the o,p-product, the position isomer of bisphenol M ($\alpha$-(4-hydroxyphenyl)-$\alpha$-(2-hydroxyphenyl)-1,3-diisopropylbenzene, 3.95 g, yield 12%), were obtained. After completion of the same aftertreatment and purification operations employing toluene as in Example 3, bisphenol M was isolated (17.1 g., isolation yield 52%, purity 99.6%).

EXAMPLE 16

A 500-ml three-neck reactor was charged with Amberlist-15(7.5 g, 2.6 mmols), phenol(178.5 g, 633 mmols) and toluene(60 ml). The contents were heated up to 80° C. in nitrogen atmosphere. Under agitation, a mixture of m-isopropenylbenzene(4.22 g, 31.5 mmols) and toluene(30 ml) was fed thereto over 3 hours at 80° C. After completion of feed, agitation was carried out at 80° C. for 10 minutes and then amberlist-15 was removed by filtration. The filtrate was analyzed by liquid chromatography. Bisphenol-A(m,p) (2-(3-hydroxyphenyl)-2-(4-hydraxyphenyl 6.46 g, 28.4 mmols, yield 90%), the intended product, was obtained. After completion of the same aftertreatment and purification operations as those in example 3, bisphenol A (m,p) was isolated(5.03 g., isolated yield 70%, purity 99.6%).

What is claimed is:

1. A process for the production of bisphenol compound comprising:

a step for reacting a phenolic compound (a) with at least one compound (b) selected from the group consisting of dialkenylbenzene compounds, bis(hydroxyalkyl) benzene compounds and (hydroxyalkyl)-alkenylbenzene compounds or at least one compound (c) selected from the group consisting of monoalkenylphenolic compounds and mono(hydroxyalkyl) phenolic compounds in the presence of an acidic catalyst to obtain a reaction mixture containing said bisphenol compound, a step for neutralizing said reaction mixture with an anion exchange resin wherein said step for neutralizing is carried out in at least one solvent selected from the group consisting of aromatic hydrocarbon compounds and aliphatic hydrocarbon compounds, a step for removing the phenolic compound remaining in said reaction mixture to concentrate said neutralized reaction mixture, and a step for isolating said bisphenol compound from the resulting concentrated mixture.

2. A process claimed in claim 1, wherein said acidic catalyst is a cation exchange resin.

3. A process claimed in claim 1, wherein said reaction is carried out in at least one solvent selected from the group consisting of aromatic hydrocarbon compounds and aliphatic hydrocarbon compounds.

4. A process claimed in claim 1, wherein said anion exchange resin is an ion exchange resin having at least one basic group selected from the group consisting of amino groups and quaternary ammonium salts.

5. A process claimed in claim 1, wherein said isolation is carried out by crystallization.

6. A process claimed in claim 4, wherein toluene or xylene is used as the solvent of said crystallization.

\* \* \* \* \*

UNITED STATES PATENT AND TRADEMARK OFFICE
CERTIFICATE OF CORRECTION

PATENT NO. : 6,316,677 B1
DATED : November 13, 2001
INVENTOR(S) : Masahiro Enna et al.

It is certified that error appears in the above-identified patent and that said Letters Patent is hereby corrected as shown below:

<u>Title page,</u>
Item [56], FOREIGN PATENT DOCUMENTS, add -- DD153680 A 1/27/82 (DE) --

Signed and Sealed this

Twenty-ninth Day of October, 2002

*Attest:*

JAMES E. ROGAN
*Attesting Officer*     *Director of the United States Patent and Trademark Office*